United States Patent
Bratz et al.

(10) Patent No.: US 6,218,337 B1
(45) Date of Patent: Apr. 17, 2001

(54) SOLID MIXTURES OF 3-ISOPROPYL-2,1,3-BENZOTHIADIAZIN-4-ONE-2,2,-DIOXIDE OR ITS SALTS

(75) Inventors: Matthias Bratz; Karl-Friedrich Jäger, both of Limburgerhof; Rainer Berghaus, Speyer; Adolf Parg, Bad Dürkheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/269,334

(22) PCT Filed: Sep. 12, 1996

(86) PCT No.: PCT/EP97/05002
 § 371 Date: Mar. 25, 1999
 § 102(e) Date: Mar. 25, 1999

(87) PCT Pub. No.: WO98/12922
 PCT Pub. Date: Apr. 2, 1998

(30) Foreign Application Priority Data

Sep. 27, 1996 (DE) .................................... 19639839

(51) Int. Cl.$^7$ .................................... A01N 43/72
(52) U.S. Cl. .......................... 504/131; 504/222
(58) Field of Search ...................... 504/131, 222

(56) References Cited

U.S. PATENT DOCUMENTS

| 3,708,277 | 1/1973 | Zeidler et al. ........................... 71/91 |
| 3,888,655 | 6/1975 | Fischer ..................................... 71/91 |
| 4,557,751 | 12/1985 | Ronning et al. ......................... 71/91 |
| 5,266,553 | 11/1993 | Champion et al. ................... 504/206 |
| 5,280,008 | 1/1994 | Cahoy et al. ......................... 504/116 |
| 5,356,861 | 10/1994 | Gednalski et al. ................... 504/206 |
| 5,629,179 | 5/1997 | Mierendorf et al. ............... 435/91.2 |

FOREIGN PATENT DOCUMENTS

| 1 167 270 | 9/1987 | (CA) . |
| 238 240 | 9/1987 | (EP) . |
| 1 405 638 | 9/1975 | (GB) . |
| 2 225 943 | 6/1990 | (GB) . |
| 93/22917 | 11/1993 | (WO) . |
| 94/09627 | 5/1994 | (WO) . |
| 94/28712 | 12/1994 | (WO) . |
| 95/28410 | 10/1995 | (WO) . |
| 9528410 * | 10/1995 | (WO) . |

OTHER PUBLICATIONS

Weed Res. 1984, vol. 24, 67–77.
5–Agrochemicals, vol. 113, 1990, p. 259.
Chem. Abst. vol. 113, 1990 186502.

* cited by examiner

Primary Examiner—Jose' G. Dees
Assistant Examiner—Alton Pryor
(74) Attorney, Agent, or Firm—Keil & Weinkauf

(57) ABSTRACT

A solid mixture comprising

A) 3-isopropyl-2,1,3-benzothiadiazine-4-one 2,2-dioxide or a salt thereof and

B) at least one nonionic surfactant, a process for its preparation, and its use for controlling undesirable vegetation.

16 Claims, No Drawings

SOLID MIXTURES OF 3-ISOPROPYL-2,1,3-BENZOTHIADIAZIN-4-ONE-2,2,-DIOXIDE OR ITS SALTS

This application is a 371 of PCT/EP97/05002 filed Sep. 12, 1996.

The present invention relates to a solid mixture comprising

A) 3-isopropyl-2,1,3-benzothiadiazin-4-one 2,2-dioxide or a salt thereof and

B) at least one nonionic surfactant.

The present invention furthermore relates to a process for the preparation of this solid mixture, the use of the solid mixture is and method of controlling undesirable vegetation.

Liquid formulations are established in the field of agriculture, and surfactants are added under practical conditions when controlling harmful plants for increasing the herbicidal activity of the active ingredient and for guaranteed weed control.

The disadvantage of liquid formulations is that large amounts of packaging material, such as canisters made of metal and man-made materials, are accumulated and have to be disposed of in a safe manner. Furthermore, the safe storage of products in liquid form is complicated. Low storage temperatures may also result in undesirable crystallization.

Benzothiadiazin-4-one 2,2-dioxides and salts thereof are disclosed in the literature as herbicidally active crop protection substances (DE-A 15 42 836, DE-A 21 64 459, DE-A 22 17 722).

The earlier German Patent Application with the file number 196 13 395.5 describes granules of hygroscopic water-soluble products, for example the sodium salt of 3-isopropyl-2,1,3-benzothiadiazin-4-one 2,2-dioxide. These granules are preferably used without auxiliaries and additives.

DE-A 43 15 878 describes the solid, non-hygroscopic magnesium salt of 3-isopropyl-2,1,3-benzothiadiazin-4-one 2,2-dioxide. This publication also teaches a solid mixture of this salt and of sodium lignosulfonate which is solid per se and acts as dispersant.

It is an object of the present invention to provide further solid mixtures which are based on 3-isopropyl-2,1,3-benzothiadiazin-4-one 2,2-dioxide or a salt thereof and which additionally have a good biological activity.

We have found that this object is achieved by a solid mixture comprising

A) 3-isopropyl-2,1,3-benzothiadiazin-4-one 2,2-dioxide or a salt thereof and

B) at least one nonionic surfactant.

We have furthermore found a process for the preparation of this solid mixture, and also the use of the solid mixture and a method of controlling undesirable vegetation.

Suitable salts of 3-isopropyl-2,1,3-benzothiadiazin-4-one 2,2-dioxide are the alkali metal salts, especially the sodium and the potassium salt, the alkaline earth metal salt, especially the calcium, the magnesium and the barium salt, the transition metal salts, especially the manganese, the copper, the zinc and the iron salt, the ammonium salts, in which up to 4 hydrogen atoms can be replaced by $C_1$–$C_4$-alkyl or hydroxy-$C_1$–$C_4$-alkyl and/or a phenyl or benzyl, especially the ammonium, the diisopropyl-ammonium and the tetramethylammonium salt.

Particularly preferred are the sodium, the magnesium and the ammonium salt.

The preparation of 3-isopropyl-2,1,3-benzothiadiazin-4-one 2,2-dioxide and the salts thereof is generally known (cf. DE-A 15 42 836, DE-A 43 15 878 and DE-A 195 05 036).

The nonionic surfactants are alcohol alkoxylates, alkylated EO/PO block polymers, alkylphenol ethoxylates, polyols, EO/PO block polymers, organosilicone [sic] compounds, alkyl glycosides, alkyl polyglycosides, fatty amine alkoxylates, dialkyl adipates and dialkyl phthalates.

Especially preferred amongst the nonionic surfactants are alcohol alkoxylates, alkylated EO/PO block copolymers, EO/PO block polymers, organosilicon compounds, alkyl glycosides, alkyl polyglycosides, fatty amine alkoxylates, dialkyl adipates and dialkyl phthalates.

Particularly preferred are alcohol alkoxylates, alkylated EO/PO block polymers, EO/PO block copolymers, alkyl glycosides, alkyl polyglycosides, fatty amine alkoxylates, dialkyl adipates and dialkyl phthalates.

Especially preferred amongst the nonionic surfactants are also alkyl glycosides and alkyl polyglycosides, mainly alkyl polyglycosides. Suitable substances which are preferred are alkyl polyglycosides with a mean degree of polymerization of 1.0 to 1.7. Additionally preferred are alkyl polyglycosides with a $C_6$–$C_{18}$-alkyl chain.

Examples of alcohol alkoxylates are, inter alia, Lutensol® ON, Lutensol®TO, Lutensol® AO, Lutensol®AT (BASF); Genapol® brands (Hoechst AG) and Synperionic® brands (ICI); Lutensol® ON 30 is preferably used.

Examples of alkylated EO/PO block polymers are, inter alia, Antarox® BO (Rhône-Poulenc); Emulsogen® V 2436 (Hoechst AG), Plurafac LF 700 (BASF AG); Dehypon® LS, Dehypon® LT (Henkel); and Synperionic® LF brands (ICI).

Examples of EO/PO block polymers are, inter alia, Pluronic® PE brands (BASF); Genapol® PF brands (Hoechst AG) and Synperionic® PE brands (ICI).

Examples of organosilicon compounds are, inter alia, Silwet® L-77 (Witco) and Tegopren® brands (Goldschmidt).

Examples of alkyl glycosides and alkyl polyglycosides are, inter alia, AG 6202 (Akzo Nobel); Lutensol® GD 70 (BASF AG); Atplus® 258, Atplus® 264, Atplus® 430, Atplus® 460, Atplus® 469, Atplus® 450 (ICI Surfactants); Agrimul® PG 2067, Agrimul® PG 2069", Agrimul® PG 600", Agrimul PG 215" (Henkel).

Examples of fatty amine alkoxylates are, inter alia, Ethomeen® brands, Armoblem® brands (Akzo-Nobel) and Genamin® brands (Hoechst).

Examples of dialkyl adipates are dioctyl adipate and diisotri-decyl adipate.

An example of dialkyl phthalate which may be mentioned is diisotridecyl phthalate.

The brands (trade names) given in the abovementioned examples do not represent any restriction; they are merely representatives of the particular class of substances. Other brands (trade names) are given in the following publications:

McCutheon's; Emulsifiers and Detergents, Volume 1: Emulsifiers and Detergents 1994, North American Edition, McCutheon Division, Glen Rock N.J., USA;

McCutheon's; Emulsifiers and Detergents, Volume 2: Emulsifiers and Detergents 1994, International Edition, McCutheon Division, Glen Rock N.J., USA;

Surfactants in Europe, A Directory of surface active agents available in Europe, 2nd Ed. 1989, Terg Data, Darlington, England; Ash, Michael, Handbook of cosmetic and personal care additives, 1994, Gower Publishing Ltd, Aldershot, England;

Ash, Michael, Handbook of industrial Surfactants, 1993, Gower Publishing Ltd, Aldershot, England.

The mixture according to the invention may furthermore comprise at least one water-soluble inorganic salt from amongst the group consisting of ammonium salts, alkali metal salts and alkaline earth metal salts.

Suitable inorganic water-soluble ammonium salts are ammonium compounds, or else urea and thiourea.

Examples of water-soluble inorganic alkali metal salts which can be employed are sodium and potassium salts.

Suitable water-soluble inorganic alkaline earth metal salts are calcium and magnesium salts, especially preferably magnesium salts.

Particularly preferred as water-soluble inorganic ammonium salts are, inter alia, ammonium sulfate, ammonium hydrogen sulfate, ammonium chloride, ammonium acetate, ammonium formate, ammonium oxalate, ammonium carbonate, ammonium hydrogen carbonate, ammonium nitrate, ammonium thiosulfate, ammonium phosphate, ammonium hydrogen diphosphate, ammonium hydrogen monophosphate, ammonium hydrogen phosphate and ammonium thiocyanate. Ammonium sulfate is very especially preferably used.

The mixture according to the invention may furthermore comprise at least one other customary formulation auxiliary. Suitable customary formulation auxiliaries are, inter alia, dispersants, wetting agents, binders, antifoam agents, chelating agents and lubricants.

The dispersants and wetting agents which are suitable are anionic, cationic, amphoteric or nonionic. Preferred are anionic wetting agents, such as condensates of aromatic sulfonic acids and formaldehyde, lignosulfonates and their sodium, potassium and ammonium salts, alkylsulfonates and polyoxyethylene fatty acid esters, polyoxyethylene fatty alcohol ethers, EO/PO block polymers and the like.

Suitable binders (adhesives) are, in particular, polyvinyl-pyrrolidone, polyvinyl alcohol, polyvinyl acetate, vinylpyrrolidone/vinyl acetate copolymers, carboxymethylcellulose, starch and dextrins.

Examples of suitable antifoam agents are silicone oils or silicone oil emulsions, long-chain alcohols, fatty acids and salts thereof, organofluorin compounds, acetylene alcohols and mixtures of these. Substances which are preferably employed are silicone oils, silicone oil emulsions and long-chain alcohols.

Examples of suitable chelating agents are salts of ethylene-diaminetetraacetic acid, salts of nitrilotriacetic acid, salts of polyphosphoric acids and mixtures of these.

Suitable lubricants are, inter alia, magnesium stearate, sodium stearate, talc, polyethylene glycols and mixtures of these.

The following embodiments of the solid mixture according to the invention are preferred:

1) In a preferred embodiment, the mixture according to the invention comprises, as component A, the sodium, magnesium or ammonium salt of 3-isopropyl-2,1,3-benzothiadiazin-4-one 2,2-dioxide and, as component B, at least one nonionic surfactant or mixtures of these.

Especially preferred in this context are the mixtures which comprise, as component B, an alkyl glycoside or alkyl polyglycoside. Substances which are particularly suitable are alkyl polyglycosides with a degree of polymerization of 1.0 to 1.7. Also preferred are alkyl polyglycosides having $C_6$–$C_{18}$-alkyl chains. Examples of suitable alkyl polyglycosides are AG 6206 (Akzo Nobel), Lutensol® GD70 (BASF AG), Atplus® 258, Atplus® 264, Atplus® 430, Atplus® 460, Atplus® 469, Atplus® 450 (ICI Surfactants), Agrimul® PG 2067, Agrimul® PG 2069", Agrimul® PG 600", Agrimul® PG 215" (Henkel).

2) In another preferred embodiment, the mixture according to the invention comprises, as component A, the sodium, magnesium or ammonium salt of 3-isopropyl-2,1,3-benzothiadiazin-4-one 2,2-dioxide, as component B at least one surfactant or mixtures of these and furthermore at least one nonionic water-soluble inorganic ammonium, alkali metal or alkaline earth metal salt or mixtures of these.

The mixture according to the invention preferably comprises, as water-soluble inorganic ammonium, alkali metal or alkaline earth metal salt, an ammonium salt.

Especially preferred in this context are mixtures which comprise, as component B, at least one alkyl glycoside or alkyl polyglycoside, or mixtures of these.

Very especially preferably suitable as ammonium salt is ammonium sulfate.

Most preferred in this context are mixtures which comprise, as component B, an alkyl polyglycoside or mixtures of these.

Utmost preference in this context is given to mixtures which comprise, as component A, the sodium salt of 3-isopropyl-2,1,3-benzothiadiazin-4-one 2,2-dioxide.

3) In another preferred embodiment, the mixture according to the invention comprises, as component A, the sodium, magnesium or ammonium salt of 3-isopropyl-2,1,3-benzothiadiazin-4-one 2,2-dioxide, as component B at least one nonionic surfactant or mixtures of these and furthermore at least one additional customary formulation auxiliary as mentioned above, or mixtures of these.

The mixtures according to the invention preferably comprise, as additional formulation auxiliary, one or more antifoam agents.

The mixtures according to the invention especially preferably comprise, as component B, at least one alkyl glycoside or alkyl polyglycoside or mixtures of these.

The substances which are very especially preferably employed as antifoam agents are silicone oils, silicone oil emulsions, long-chain alcohols and mixtures of these.

Most preferred in this context are mixtures which comprise, as component B, an alkyl polyglycoside or mixtures of these.

4) In another preferred embodiment, the mixture according to the invention comprises, as component A, the sodium, magnesium or ammonium salt of 3-isopropyl-2,1,3-benzothiadiazin-4-one 2,2-dioxide, as component B at least one nonionic surfactant or mixtures of these and furthermore at least one water-soluble inorganic ammonium, alkali metal or alkaline earth metal salt and an additional formulation auxiliary or mixtures of these.

Preferred in this context are mixtures which comprise, as water-soluble ammonium, alkali metal or alkaline earth metal salt, an ammonium salt or mixtures of these.

Additional formulation auxiliaries which are especially preferably employed in such mixtures are antifoam agents.

The substances which are also particularly suitable as components B are alkyl polyglycosides, as ammonium salt ammonium sulfate and as antifoam agents, for example, silicone oils, silicone oil emulsions or long-chain alcohols.

Very especially preferred in this context are mixtures which comprise, as component A, the sodium salt of 3-isopropyl-2,1,3-benzothiadiazin-4-one 2,2-dioxide.

The abovementioned preferred embodiments of the mixtures according to the invention may additionally comprise colors, preservatives and other active ingredients used in crop protection.

The substances which are particularly suitable as other active ingredients used in crop protection are herbicidally and growth-regulatory active compounds, eg. 1,2,4-thiadiazoles, 1,3,4-thiadiazoles, amides, aminophosphoric acid and its derivatives, glyphosate, glyphosinate, aminotriazoles, anilides, (het)aryloxyalkanoic acid and its derivatives, benzoic acid and its derivatives, benzothiadiazinones, triketones, hetaryl aryl ketones, benzylisoxazolidinones, meta-$CF_3$-phenylpyridines, carbamates, quinoline [sic] acid and its derivatives, chloroacetanilides, cyclohexanedione oxime ethers, diazines, dichloropropionic acid and its derivatives, dihydrobenzofurans, dihydrofuran-3-ones, dinitroanilines, dinitrophenols, diphenyl ethers, dipyridyls, halocarboxylic acids and their derivatives, ureas, N-phenyluracils, imidazoles, imidazolinones, isoindolediones, oxadiazoles, oxiranes, phenols, aryloxy- or hetaryloxyphenoxypropionic esters, phenylacetic acid and its derivatives, phenylpropionic acid and its derivatives, pyrazoles, phenylpyrazoles, pyridazines, pyridinecarboxylic acid and its derivatives, pyrimidyl ethers, sulfonamides, sulfonylureas, triazines, triazinones, triazolinones, triazolecarboxamides, triketones, 4H-1,3-benzoxazines, N-phenylcarbamates and thiocarbamates. The following are preferably suitable as additional active ingredients used in crop protection: glyphosate, (het)aryloxyalkanoic acid and its derivatives, benzoic acid and its derivatives, triketones, hetaryl aryl ketones, quinoline [sic] acid and its derivatives, cyclohexanedione oxime ethers, dichloropropionic acid and its derivatives, dinitroanilines, diphenyl ethers, dipyridyls, halocarboxylic acids and their derivatives, ureas, imidazolinones, phenols, aryloxy- or hetaryloxyphenoxypropionic esters, phenylacetic acid and its derivatives, phenylpropionic acid and its derivatives, pyridazines, pyridinecarboxylic acid and its derivatives, sulfonamides and sulfonylureas.

As a rule, the constituents of the mixture according to the invention are employed in the form of the technical-grade product in question.

As a rule, component A amounts to 0.5 to 90, preferably 10 to 85 and particularly 40 to 85% by weight of the mixture according to the invention, based on the finished mixture.

Component B normally amounts to 3 to 40, preferably 3 to 25% by weight, based on the finished mixture.

If the mixture according to the invention additionally comprises a water-soluble inorganic ammonium salt or mixtures of these salts, they amount, as a rule, to 5 to 60, in particular 5 to 50, % by weight based on the finished mixture.

When preparing the mixture according to the invention, the starting material used is, as a rule, 3-isopropyl-2,1,3-benzothiadiazin-4-one 2,2-dioxide or a salt thereof.

In the case of the salts of 3-isopropyl-2,1,3-benzothiadiazin-4-one 2,2-dioxide, the technical-grade active ingredient is mixed intimately with the nonionic surfactant, with the ammonium, alkali metal or alkaline earth metal salts which may be added, with the additional formulation auxiliaries which may be present and, if appropriate, with water. All components can be mixed with each other in one step; however, it is also possible to admix the components one after the other.

If appropriate, the resulting crude mixture is treated with more water so that an extrudable material is formed. This is subsequently extruded. Basket extruders, radial extruders or dome extruders in which the granule undergoes little compaction are preferably used for this purpose. The granules which have thus been obtained by means of extruder granulation, are dried and, if appropriate, screened.

3-Isopropyl-2,1,4-benzothiadiazin-4-one 2,2-dioxide as such is mixed with the surfactant, with the ammonium, alkali metal or alkaline earth metal salts which may be added, with the additional formulation auxiliaries which may be present and, if appropriate, water and a proton acceptor such as sodium hydroxide, potassium hydroxide, sodium hydrogen carbonate, potassium hydrogen carbonate, calcium carbonate, magnesium oxide, sodium phosphate, potassium phosphate, sodium silicate or alkali metal salts of di-, tri- or polyphosphoric acids, or mixtures of these. All components can be mixed with each other in one step; however, it is also possible to mix the components one after the other.

If appropriate, the resulting crude mixture is treated with more water so that an extrudable material is formed and this is subsequently extruded. Basket extruders, radial extruders or dome extruders in which the granule undergoes little compaction are preferably used for extrusion.

The resulting granules are dried and, if appropriate, screened. The proton acceptor is expediently employed in an equimolar ratio based on the technical-grade active ingredient. However, it may be advantageous to employ an excess or a substoichiometric amount of proton acceptor.

Equally, it is possible to carry out a fluidized-bed granulation. To this end, an aqueous solution, emulsion or suspension of the mixture according to the invention is sprayed and agglomerated in a fluidized-bed granulation apparatus.

However, it is also possible to introduce solid constituents of the mixture according to the invention into the apparatus and to spray them with a solution, emulsion or suspension of the remaining constituents of the mixture according to the invention, thus agglomerating them.

Furthermore suitable for preparing the mixtures according to the invention are spray-drying, mixer granulation and disk is granulation.

The resulting mixtures according to the invention are distinguished by good dissolution behavior in water.

The mixtures according to the invention are suitable for controlling undesirable vegetation by treating the seeds, the plants or their environment with a herbicidally active amount of the mixture according to the invention.

The purpose of the surfactants is to assist the biological activity of 3-isopropyl-2,1,3-benzothiadiazin-4-one 2,2-dioxide or salts thereof by promoting wetting and/or transport of the active ingredient on the surface and within the plant.

To apply the mixture according to the invention, a procedure is normally followed in which they are generally first mixed with 25 to 1000 times, preferably 50 to 200 times, the amount of water. The spray mixture is then applied to the target plants and/or into their environment, in particular pre- or post-emergence. As an alternative or in addition to this, the seeds of the target plant may also be treated in an appropriate manner prior to sowing.

If the active ingredient mixtures, which can be obtained by dilution with water, are less well tolerated by certain crop plants, application techniques may be used in which the spray mixtures are sprayed, with the aid of the spraying equipment, in such a way that the leaves of the sensitive crop plants come into as little contact as possible, if any, with the active ingredients, while the active ingredients reach the leaves of the undesirable plants which grow underneath, or the bare soil (post-directed, or lay-by, application).

The rate of application of 3-isopropyl-2,1,3-benzothiadiazin-4-one 2,2-dioxide or a salt thereof in the form of the mixture according to the invention are from 0.5 to 7, preferably 0.5 to 5, in particular 1 to 3, kg/ha of cultivated area, depending on the purpose of the control measures, the season, the target plant and its growth stage.

PREPARATION EXAMPLES

Example 1

58.8 g of Na$^\oplus$ salt of 3-isopropyl-2,1,3-benzothiadiazin-4-one 2,2-dioxide (Na$^\oplus$-bentazone) and 5.8 g of Lutensol® GD 70 (BASF AG) were mixed intimately in a Moulinette kitchen blender. The resulting bulk was extruded by means of an extruder (KAR-75, Fitzpatrick, aperture size 0.8 mm) and subsequently dried in a drying oven at 60° C.

Example 2

52.5 g of NH$_4^\oplus$-bentazone and 10.9 g of Lutensol® GD 70 (BASF AG) were mixed intimately in a Moulinette kitchen blender. The resulting bulk was extruded as described in Example 1.

Example 3

52.5 g of NH$_4^\oplus$-bentazone and 8.2 g of AG 6202 (ethylhexyl glucoside, Akzo) were mixed intimately in a Moulinette kitchen blender. The resulting bulk was extruded as described in Example 1.

Example 4

169.2 g of dry Na$^\oplus$-bentazone, 36.0 g of Lutensol® GD 70, 88.8 g of ammonium sulfate and 6.0 g of antifoam SRE were homogenized in a food processor (Kenwood Chef) while adding 36.0 g of water, and the bulk was subsequently extruded in a dome extruder (DGL-1, Fitzpatrick, aperture diameter 0.5 mm).

Example 5

169.2 g of dry Na$^\oplus$-bentazone, 36.0 g of Lutensol® GD 70, 88.8 g of ammonium sulfate and 6.0 g of silicone emulsion SLE (Wacker) were homogenized in a food processor (Kenwood Chef) while adding 36.0 g of water, and the bulk was subsequently extruded in a dome extruder (DEL-1, Fitzpatrick, aperture diameter 0.5 mm).

Example 6

59.0 g of dry Na$^\oplus$-bentazone, 10.0 g of Lutensol® GD 70, 27.0 g of ammonium sulfate and 2.0 g of isotridecanol are mixed intimately in a food processor (Kenwood Chef), and the bulk is subsequently extruded.

Example 7

A spray mixture was prepared from 410.5 g of a 50% by weight aqueous Na$^\oplus$-bentazone solution and 28.85 g of Silwet® L77 (silicone polyether copolymer, OSI).

65.7 g of crystalline ammonium sulfate with a particle size of less than 0.5 mm were introduced into a laboratory fluidized-bed granulator. A two-substance nozzle was located above the fluidized bed. The granules which had been introduced were fluidized using air at an input temperature of 120° C. The spray pressure was set at 2.1 bar. The spray mixture was sprayed into the fluidized bed, and the water evaporated.

At the end of the granulation process, granules comprising 60% by weight of bentazone and 5.7% by weight of Silwet® L77 were obtained.

Example 8

1724.0 g of dry Na$^\oplus$-bentazone were dissolved in 1350.0 g of distilled water. 300.0 g of AG® 6202 (alkyl polyglucoside, Akzo) in the form of a 65% by weight aqueous solution were then incorporated and the mixture was used as spray solution. 465.0 g of crystalline ammonium sulfate with a particle size of less than 0.5 mm were introduced into a laboratory fluidized-bed granulator (MP1, Niro-Aeromatic). A two-substance nozzle was located above the fluidized bed. The granules which had been introduced were fluidized using air at an input temperature of 120° C. The spray pressure of the two-substance nozzle was set at 3 bar. The spray solution was sprayed into the fluidized bed, and the water evaporated Granules comprising 61.5% by weight of Na$^\oplus$-bentazone, 8% by weight of alkyl polyglucoside and 1% of residual moisture were obtained.

Example 9

50.7 g of Na$^\oplus$-bentazone, 8.8 g of Lutensol® GD 70, 8.5 g of sodium hydroxide and 2.8 g of distilled water were introduced into an IKA® laboratory mill and mixed intimately. A reaction started, during which Na$^\oplus$-bentazone was formed. The resulting viscous bulk was treated with 29.2 g of ammonium sulfate, and a further 13.2 ml of water were added a little at a time. This resulted in a moist bulk which was extruded by means of an extruder (KAR-75, Fitzpatrick, aperture size 0.8 mm). The resulting granules were dried in a drying oven at 60° C.

Example 10

25.4 g of Na$^\oplus$-bentazone, 4.2 g of sodium hydroxide, 1.8 g of Pluronic® PE 6400 (BASF) and 1.4 g of water were mixed intimately in an IKA® laboratory mill until a noticeable heat tone was observed. 17.2 g of ammonium sulfate and a further 13.5 ml of water were then added. The resulting bulk was extruded and dried as in Example 8.

Example 11

In a kneader (Werner & Pfleiderer, LUK 0,75 Vak), 303.0 g of bentazone, 72.0 g of Lutensol® GD 70, 60.0 g of sodium hydroxide, 150.0 g of ammonium sulfate, 6.0 g of antifoam SRE and 8.4 ml of water were premixed, homogenized and extruded as described in Example 8.

The mixtures according to the invention obtained in Examples 1 to 3 and 7 to 9 dissolve or disperse in water in the course of two minutes to give a clear solution or dispersion.

Use Example

The enhanced activity of herbicidally active ingredients used in crop protection, by means of the mixtures according to the invention, was demonstrated by experiments in the greenhouse and in the open.

When carrying out experiments in the greenhouse, it was important to maintain defined growth and treatment conditions in order to tell the difference between effects.

In the greenhouse, the seeds of the test plants were sown separately for each species into plastic pots of diameter approximately 12 cm using a peaty substrate.

In the case of pre-emergence treatment, the active ingredients which were suspended or emulsified in water were applied directly after sowing by means of finely distributing nozzles. The containers were irrigated gently to promote germination and growth, and they were subsequently covered with transparent plastic hoods until the plants had rooted. This cover causes [sic] uniform germination of the test plants, unless this was adversely affected by the active ingredients.

For the purpose of post-emergence treatment, the test plants were first grown to a height of 3 to 15 cm, depending on the plant habit, and then treated with a mixture according to the invention which was dissolved, suspended or emulsified in water. To this end, the test plants were either sown directly and grown in the same containers, or they were first grown separately as seedlings and transplanted into the test containers a few days prior to treatment.

The plants were kept at from 10 to 25 or 20 to 35° C., depending on the species. The test period extended over 2 to 4 weeks. During this time, the plants were tended, and their response to the individual treatments was evaluated.

A similar protocol was followed for experiments in the open or under conditions resembling open conditions. The crop plants and typical relevant undesirable plant species were sown or planted in parallel rows.

In some cases, naturally occurring plant populations were also included in the investigations. In certain cases, plants were also grown in pots under conditions resembling open conditions.

The evaluation was carried out using a scale of from 0 to 100. "100" means no plant emergence or complete destruction of at least the aerial parts, while "0" means no damage or normal course of growth.

We claim:

1. A solid mixture comprising
   A) a salt of 3-isopropyl-2,1,3-benzothiadiazin-4-one 2,2-dioxide and
   B) at least one alkyl glycoside or alkyl polyglycoside.

2. A solid mixture as defined in claim 1 which furthermore comprises at least one water-soluble inorganic salt from amongst the following group: ammonium salt, alkali metal salt or alkaline earth metal salt.

3. A solid mixture as defined in claim 2 in which the water-soluble inorganic ammonium salt is ammonium sulfate.

4. A solid mixture as defined in claim 1 which comprises 0.5 to 90% by weight of component A.

5. A solid mixture as defined in claim 1 which comprises 3 to 40% by weight of component B.

6. A process for the preparation of a solid mixture as defined in claim 1 which comprises mixing the components and granulating the resulting mixture.

7. A method of controlling undesirable vegetation which comprises treating the seeds, the plants or their environment with a herbicidally active amount of the solid mixture as defined in claim 1.

8. The solid mixture of claim 1, wherein component A is the sodium, magnesium or ammonium salt of 3-isopropyl-2,1,3-benzothiadiazin-4-one-2,2-dioxide.

9. The solid mixture of claim 1, wherein component A is the sodium salt of 3-isopropyl-2,1,3-benzothiadiazin-4-one-2,2-dioxide.

10. The solid mixture of claim 1, wherein component B comprises an alkul polyglycoside having a degree of polymerization of 1.0 to 1.7.

11. The solid mixture of claim 1, wherein component B comprises an alkyl polyglycoside having an alkyl chain of $C_6$–$C_{18}$.

12. A solid mixture as defined in claim 3, wherein component A is the sodium salt of 3-isopropyl-2,1,3-benzothiadiazin-4-one-2,2-dioxide.

13. A solid mixture as defined in claim 3, wherein component B comprises an alkyl polyglycoside having a degree of polymerization of 1.0 to 1.7.

14. A solid mixture as defined in claim 3, wherein component B comprises an alkyl polyglycoside in which the alkyl group has from 6 to 18 carbon atoms.

15. A solid mixture as defined in claim 3, wherein component B comprises an alkyl polyglycoside having a degree of polymerization of 1.0 to 1.7 and a $C_6$–$C_{18}$ chain.

16. A solid mixture as defined in claim 3, wherein component A is the sodium salt of 3-isopropyl-2,1,3-benzothiadiazin-4-one-2,2-dioxide and component B comprises an alkyl polyglycoside having a degree of polymerization of 1.0 to 1.7 and an alkyl chain of 6 to 18 carbons.

* * * * *

UNITED STATES PATENT AND TRADEMARK OFFICE
CERTIFICATE OF CORRECTION

PATENT NO. : 6,218,337 B1
DATED : April 17, 2001
INVENTOR(S) : Bratz et al.

Page 1 of 1

It is certified that error appears in the above-identified patent and that said Letters Patent is hereby corrected as shown below:

<u>Title page,</u>
Item [22], "Sep. 12, 1996" should be -- Sep. 12, 1997 --.

<u>Column 10, claim 10,</u>
Line 18, "alkul" should be -- alkyl --.

Signed and Sealed this

Sixth Day of November, 2001

Attest:

NICHOLAS P. GODICI
Attesting Officer
Acting Director of the United States Patent and Trademark Office